(12) United States Patent
Gorinshteyn et al.

(10) Patent No.: US 11,058,615 B1
(45) Date of Patent: Jul. 13, 2021

(54) COSMETIC DERMAL SERUM WITH SKIN REJUVENATION PROPERTIES

(71) Applicant: Key Element LLC, Rolling Hills Estates, CA (US)

(72) Inventors: Boris Gorinshteyn, Roswell, GA (US); Donna Kasseinova, Palos Verdes Estates, CA (US)

(73) Assignee: Key Element LLC, Rolling Hills Estate (CA)

( * ) Notice: Subject to any disclaimer, the term of this patent is extended or adjusted under 35 U.S.C. 154(b) by 295 days.

(21) Appl. No.: 16/280,118

(22) Filed: Feb. 20, 2019

Related U.S. Application Data

(60) Provisional application No. 62/637,650, filed on Mar. 2, 2018.

(51) Int. Cl.
| | |
|---|---|
| *A61K 36/00* | (2006.01) |
| *A61K 8/04* | (2006.01) |
| *A61K 8/34* | (2006.01) |
| *A61Q 19/08* | (2006.01) |
| *A61K 8/60* | (2006.01) |
| *A61K 8/9789* | (2017.01) |
| *A61K 8/49* | (2006.01) |

(52) U.S. Cl.
CPC ............. *A61K 8/042* (2013.01); *A61K 8/345* (2013.01); *A61K 8/4973* (2013.01); *A61K 8/608* (2013.01); *A61K 8/9789* (2017.08); *A61Q 19/08* (2013.01)

(58) Field of Classification Search
None
See application file for complete search history.

(56) References Cited

U.S. PATENT DOCUMENTS

2006/0275247 A1* 12/2006 Helman ............... A61K 8/9794
424/74
2014/0037772 A1* 2/2014 Lien ..................... A61K 36/185
424/769

* cited by examiner

*Primary Examiner* — Qiuwen Mi
(74) *Attorney, Agent, or Firm* — Bardmesser Law Group

(57) ABSTRACT

A skin rejuvenation serum includes deionized water; 3.5%-6.0% by weight Vitamin C in a form of Sodium Ascorbyl Phosphate or Magnesium Ascorbyl Phosphate; 0.5%-2.0% by weight Hyaluronic Acid in a form of low-molecular-weight Sodium Hyaluronate; 0.1%-0.3% by weight Succinic Acid in a form of Sodium Succinate; and 0.3%-1.0% by weight preservative. Optionally, the preservative is dehydroacetic acid.

9 Claims, No Drawings

COSMETIC DERMAL SERUM WITH SKIN REJUVENATION PROPERTIES

CROSS REFERENCE TO RELATED APPLICATIONS

This application claims priority to U.S. Provisional Patent Application No. 62/637,650, filed on Mar. 2, 2018.

BACKGROUND OF THE INVENTION

Field of the Invention

The present invention is related to a cosmetic serum that can rejuvenate skin by reducing appearance of signs of aging and intermediate mitigation of collagen loss via improvement in cutaneous hydration, microcirculation, metabolic stimulation, and collagen regeneration.

Description of the Related Art

Current cosmetic anti-aging formulations with hyaluronic acid in the form of sodium hyaluronate (SH) and variety of vitamin combinations, antioxidants, botanicals, oils, etc. (excluding injectable drugs or medical devices) fall short in producing real long-term results in stimulation of extracellular matrix regeneration. Visual appearance of wrinkle reduction is achieved by SH ability to retain water (humectant). Therefore, the effect is achieved by moisturizing the skin and holding the water in the deeper layers or, in other words, on the tissue level.

Accordingly, there is a need for a serum that stimulates regeneration of the collagen matrix and improves dermal metabolism.

SUMMARY OF THE INVENTION

Accordingly, the present invention is directed to a skin rejuvenation formulation. As one example of an embodiment, a skin rejuvenation serum includes deionized water; 3.5%-6.0% by weight Vitamin C in a form of Sodium Ascorbyl Phosphate or Magnesium Ascorbyl Phosphate; 0.5%-2.0% by weight Hyaluronic Acid in a form of low-molecular-weight Sodium Hyaluronate; 0.1%-0.3% by weight Succinic Acid in a form of Sodium Succinate; and 0.3%-1.0% by weight preservative. Optionally, the preservative is dehydroacetic acid.

In another embodiment, a skin rejuvenation cream, includes deionized water; 3.5%-6.0% by weight Vitamin C in a form of Sodium Ascorbyl Phosphate or Magnesium Ascorbyl Phosphate; 0.5%-2.0% by weight Hyaluronic Acid in a form of Sodium Hyaluronate low-molecular-weight; 0.1%-0.3% by weight Succinic Acid in a form of Sodium Succinate; 0.3%-1.0% by weight preservative; and an excipient. The excipient is any of: 0.05%-5.0% by weight Hydrolyzed collagen; 0.01%-5.0% by weight Allantoin; 0.01%-5.0% by weight Jade Snail Extract; 0.5%-10.0% by weight Vitamin E in a form of Tocopherol Acetate; 15-20% by weight Witch Hazel (astringent); 0.1%-5.0% by weight Urea (Moisturizer); 0.01%-1.0% by weight Barberries Extract; 0.05%-2.0% by weight Salicylic Acid; Vitamin A—50-20,000 IU/g and <2% of total weight; and 0.2%-20% by weight Glycerin.

Additional features and advantages of the invention will be set forth in the description that follows. Yet further features and advantages will be apparent to a person skilled in the art based on the description set forth herein or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

DETAILED DESCRIPTION OF EMBODIMENTS OF THE INVENTION

Reference will now be made in detail to the embodiments of the present invention.

The objective is to produce a formulation that reduces appearance of wrinkles and fine lines, and reduces visible signs of aging. The formulation is generally targeted to adults over 40, both male and female (for age-related and rejuvenative use) and to people age 12-21 who suffer from teenage acne, although the intended use is not limited to these groups.

As people age, the skin becomes a biological canvas that depicts a person's diet, lifestyle, ailments, and health deterioration. Since the skin is the largest organ of human body, and one that can be seen and touched, human mental perception of oneself depends, in large part, on the appearance of one's skin.

For the first time in history, modern medicine possesses sufficient knowledge of skin physiology and understanding of the aging process to slow and even reverse certain effects of aging. Hyaluronic acid (HA) is known to stimulate the restoration of the dermis by mitigation of collagen matrix via stimulating skin fibroblast. HA is a powerful humectant—it promotes retention of water in the dermis that improves skin turgor. It directly attracts and holds water molecules. Remodeling of collagen matrix and proper hydration reduce the visible signs of ageing, such as wrinkles, fine lines, and sagging skin.

Vitamin D is crucial for health and it forms in the body as a direct result of exposure to sun. Unfortunately, it comes at a price—UV rays cause accumulation of free radicals in the skin and, in turn, the inhibition of key metabolic processes that are critical to function and appearance. It promotes premature skin aging and leads to the loss of collagen and elastin.

Succinate is a unique substance that has triple mechanism of action: metabolic as part of Krebs Cycle, signaling hormone-like, and free radical scavenger—antioxidant. Sodium succinate ($Na_2C_4H_4O_4$) is a potent antioxidant that is a derivative (Salt) of succinic acid, which naturally synthesizes in every cell in our body. Sodium succinate actively blocks free radicals and stimulates metabolic processes in the skin. By improving cutaneous metabolism and reducing free radical buildup, Sodium Succinate can help significantly reduce visible signs of aging.

This synergy between sodium succinate and hyaluronic acid present as sodium Hyaluronate (($C_{28}H_{44}N_2NaO_{23}$)*n) is well studied. There are several published clinical studies on the subject in humans (all incorporated by reference in their entirety):

omicsonline.org/2155-9554/2155-9554.S1.020-032.pdf
prime-journal.com/treating-hyperpigmentation-using-a-combination-of-hyaluronic-and-succinic-acids/
aestheticsjournal.com/feature/case-study-combining-prp-ha-and-succinic-acid
prime-journal.com/combination-injectable-treatments-to-treat-the-ageing-face/ uf.ua/wp-content/uploads/2017/05/Korkunda_Lacerta.pdf

The present invention proposes to create the first dermal serum that will pair hyaluronic acid and sodium succinate (see U.S. Pat. No. 9,845,284, Method of obtaining complex acidic salts of divalent metals and dicarboxylic acids, and U.S. Pat. No. 8,933,271, Method for preparing ammonium salts of fumaric or succinic acid, both incorporated herein by reference). The composition's synergy results from ability of Hyaluronic Acid to stimulate development and growth of fibroblasts and ability of succinate to reduce free radicals in the dermis and activate signaling mechanism for stem cell migration and tissue remodeling (the sodium succinate promotes stem cell migration through the GPR91-dependent regulation of DRP1-mediated mitochondrial fission, see nature.com/articles/s41598-017-12692-x). Free radicals in the dermis suppress activity and development of fibroblasts. When concentration of free radicals is reduced, the number of active fibroblasts increases. Moreover, a metabolic effect of succinate is stimulation of cellular activity in collagen and elastin regeneration, strengthening of cellular respiration, and optimization of ion transport. By stimulating processes in the Krebs cycle, sodium succinate improves protein synthesis in the mitochondria and increases energy production. The combined effect results in significant reduction of visible signs of ageing.

Thus, a combination of three ingredients in the formulation is proposed:
1. Hyaluronic acid as Sodium Hyaluronate $((C_{28}H_{44}N_2NaO_{23})*n)$
2. Vitamin C as Sodium Ascorbyl Phosphate $(C_6H_6Na_3O_9P)$
3. Sodium Succinate Hexahydrate $(Na_2C_4H_4O_4 \times 6H_2O)$ 1. Two types of 2 Sodium Hyaluronate (SH) can be used: Low Molecular Weight (LMW, 800000-1500000 Da) and Super Low molecular weight (SLMW, 8000-15000 Da). Both types of SH (sodium hyaluronate) are used in cosmetic preparations as thickener, humectant, lubricant, and stabilizer. SH SLMW is used in formulations in the effective range from 0.1% to 10% and it is possible to extend the range for marketing claims and special purpose formulations from 0.01% to 30%. However, SH LMW can be used from 0.1% to 5%. SH LMW in the concentration of 2% or above is a super viscous gel.

2. Sodium Ascorbyl Phosphate is used as stable water-soluble form of Vitamin C. The pure natural form of Vitamin C is Ascorbic Acid $(C_6H_8O_6)$. It is used in cosmetic formulation in the range of 0.01% to 50%. Moreover, there are multiple types of Ascorbic Acid salts or derivatives both water-soluble and lipid-soluble. Magnesium Ascorbyl Phosphate $(C_6H_8M_3O_{14}P_2)$ is the most similar form of ascorbic acid salt that can be substituted for Sodium Ascorbyl Phosphate.

Other forms of Vitamin C that can generally be used in the composition are found at lpi.oregonstate.edu/mic/vitamins/vitamin-C/supplemental-forms, incorporated herein by reference in its entirety.

The combination of Sodium Hyaluronate, Vitamin C, and Sodium Succinate can be used in any topical skin treatment cosmetic or pharmaceutical: Serum, Cream, Ointment, Lotion, Toner, Tincture, etc.

3. Sodium Succinate Hexahydrate $(Na_2C_4H_4O_4 \times 6H_2O)$—Sodium Salt of Succinic Acid can also be used. There are multitude of chemical compounds deriving from Succinic Acid. It is used in water and lipid soluble forms. The range of use is from 0.001% to 50%.

Instead of Sodium Succinate, Potassium Succinate $(C_4H_4K_2O_4)$, Ammonium Succinate $(C_4H_{12}N_2O_4)$, Tocopheryl (Vitamin E) Succinate $(C_{33}H_{54}O_5)$, Magnesium Succinate $(C_4H_4MgO_4)$, etc. can be used. Generally, most water- or lipid-soluble compounds derived from succinic acid can be used to achieve the desired therapeutic effect.

The following additional ingredients can be used:

Vitamin A: Vitamin A is a group of unsaturated nutritional organic compounds that includes retinol $(C_{20}H_{30}O)$, retinal or retinaldehyde $(C_{20}H_{28}O)$, retinoic acid $(C_{20}H_{28}O_2)$, and several provitamin A carotenoids. Vitamin A has multiple functions: it is important for growth and development, for the maintenance of the immune system and good vision. Vitamin A can be used in the range from 0.001% to 5%.

Vitamin E is used as a moisturizer to treat or prevent dry, rough, scaly, itchy skin and minor skin irritations (e.g., diaper rash, skin burns from radiation therapy). Emollients are substances that soften and moisturize the skin and decrease itching and flaking. Vitamin E can be used in the range from 0.001% to pure oil.

Vitamin B can be added to the formulation. The most popular topical forms of Vitamin B Group are B3-Niacin $(C_6H_5NO_2)$, and B5 Panthothenic Acid $(C_9H_{17}NO_5)$ or Panthenol $(C_9H_{19}NO_4)$.

Thus, the proposed dermal serum is a topical cosmetic formulation with combination of low molecular weight (<50 kDa) Hyaluronic Acid and the Sodium Succinate as described in the two patents above (or any succinic acid salt or derivative that can be available to the general public for daily skin care).

The effect may be amplified if used in combination with cosmetologic procedures such as microdermabrasion, ultrasonic treatment, microneedling (see rd.com/health/beauty/microneedling-benefits/), and other procedures that may enable improved absorption.

In order to keep skin looking young, antioxidants are needed. As second line of defense, the formulation is Vitamin C. Different forms of Vitamin C can be used. There are multiple salts of ascorbic acid, including pure ascorbic acid $(C_6H_8O_6)$, that are available. The preferred form is Sodium Ascorbyl Phosphate (SAP) as the most stable water-soluble form. If a combination of SH and succinate derivatives in creams or ointments is used, a lipid soluble form of vitamin C is more suitable.

The antioxidant properties of vitamin C and its role in collagen synthesis make vitamin C an important molecule for skin health. Topical application of ascorbic acid have beneficial effects on skin cells, and several studies have shown that vitamin C may help prevent and treat ultraviolet (UV)-induced photodamage as well as enhance barrier function of the skin (see ncbi.nlm.nih.gov/pmc/articles/PMC3673383/).

It is powerful anti-aging nutrient that helps rebuild collagen. And, as added benefit, vitamin C is a good natural moisturizer.

The only downside of vitamin C in form of ascorbic acid that is has relatively short shelf life. In order to overcome stability issues, vitamin C in form of Sodium Ascorbyl Phosphate can be used, as noted above. SAP is the most stable form of bioavailable and water soluble Vitamin C (generally, any water or lipid soluble ascorbic acid salts may be used, since collagen synthesis requires presence of ascorbic acid).

In recent clinical studies it was demonstrated that SAP has significant efficacy to fight skin blemishes (see ncbi.nlm.nih.gov/pubmed/18492184).

In some people exposure to UVA and UVB may cause hyperpigmentation. SAP as demonstrated excellent efficacy in helping to normalize skin tone.

Proposed Formulation—Example 1

1. Deionized water
2. Vitamin C (as Sodium Ascorbyl Phosphate or Magnesium Ascorbyl Phosphate)—5% W/W (Weight Wise) Range 3.5%-6.0%
3. Hyaluronic Acid (as Sodium Hyaluronate low-molecular-weight)—0.5%-2.0% W/W
4. Succinic Acid (as Sodium Succinate)—0.1%-0.3% W/W
5. Dehydroacetic Acid (Preservative)—0.3%-1.0% W/W or any preservative in recommended range of use in cosmetic formulations.

Additional possible excipients for other delivery forms (creams, washes, lotions, ointments, etc.) may be:
1. Hydrolyzed collagen—0.05-5.0% WAV
2. Allantoin—0.01%-5.0% WAV
3. Jade Snail Extract—0.01%-5.0% WAV
4. Vitamin E (as Tocopherol Acetate)—0.5%-10.0% WAV
5. Witch Hazel (astringent)—15-20% WAV
6. Urea (Moisturizer)—0.1%-5.0% WAV
7. Barberries Extract 0.01%-1.0%
8. Salicylic Acid ($C_7H_6O_3$)—0.05%-5.0% WAV (For cosmetics <2% of total)
9. Vitamin A ($C_{20}H_{30}O$)—50-20,000 IU/g or <2% of total
10. Glycerin ($C_3H_8O_3$)—0.2%-20% WAV Proposed Formulation—Example 2

1. Deionized water—balance to 100%
2. Vitamin C (as Sodium Ascorbyl Phosphate)—8-10% WAV
3. Hyaluronic Acid (as Sodium Hyaluronate low-molecular-weight)—1.0%-2%
4. Succinic Acid (as Sodium Succinate Hexahydrate)—0.3%-0.5%
5. Dehydroacetic Acid (Preservative)—0.5%

Proposed Formulation—Example 3

1. Deionized water—balance to 100%
2. Vitamin C (as Magnesium Ascorbyl Phosphate)—4.5%-6.0%
3. Hyaluronic Acid (as Sodium Hyaluronate low-molecular-weight)—1.0%-20%
4. Succinic Acid (as Sodium Succinate Hexahydrate)—0.25%-0.5%
5. Dehydroacetic Acid (Preservative)—0.5%

Proposed Formulation—Example 4

1. Deionized water—balance to 100%
2. Vitamin C (as Sodium Ascorbyl Phosphate)—0.5-10%
3. Hyaluronic Acid (as Sodium Hyaluronate low-molecular-weight)—1.0%-20%
4. Succinic Acid (as Sodium Succinate Hexahydrate)—0.05%-0.5%
5. Vitamin E (as DL-Alpha Tocopheryl Acetate)—0.5-2%
6. Dehydroacetic Acid (Preservative)—0.5%

Proposed Formulation—Example 5

1. Deionized water—balance to 100%
2. Hyaluronic Acid (as Sodium Hyaluronate low-molecular-weight)—1.0-20%
3. Succinic Acid (as Sodium Succinate Hexahydrate)—0.05%-0.5%
4. Vitamin E (as DL-Alpha Tocopherol Acetate)—0.5-5.0%
5. Dehydroacetic Acid (Preservative)—0.5%

Additional excipients may include common emulsifying, thickening, and other common cosmetic ingredients. Some non-limiting examples are:

Emulsifiers: Emulsifying wax, Cetyl Alcohol ($C_{16}H_{34}O$), Cetearyl Alcohol mixture of cetyl and stearyl ($CH_3(CH_2)_nOH$) alcohols, Bees wax, Ceteareth ($CH_3(CH_2)_m(OCH_2CH_2)_nOH$) (n=2 to 100 & m=15 to 17), Polyethylene Glycol ($C_3H_8O_2$) (various), etc. (see makingcosmetics.com/Emulsifiers_c_49.html).

Thickeners that can be used are: Stearyl Palmitate ($C_{34}H_{68}O_2$), Arabic Gum, Xanthan Gum, Starch (($C_6H_{10}O_5)_n$), Hydroxyethyl Cellulose ($C_{36}H_{70}O_{19}$), etc. (see makingcosmetics.com/Thickeners_c_76.html).

Note that there is clinical confirmation that in injectable form, SH+Succinic

Acid causes regeneration of collagen and elastin cellular matrix. Thus, there is reason to believe that the serum proposed herein will be effective as well.

The serum described above can be made by dissolving all ingredients in water consecutively or in parallel with combining resulting solutions at the end. In cream form, making a cream involves multi-phase process that includes making an emulsion by combining water phase and oil phase. Making a wash involves adding a surfactant or multiple surfactants that help remove oil and dirt from the skin. Making an injectable product would involve a pharmaceutical product.

Having thus described the different embodiments, it should be apparent to those skilled in the art that certain advantages of the described formulation have been achieved.

It should also be appreciated that various modifications, adaptations, and alternative embodiments thereof may be made within the scope and spirit of the present invention. The invention is further defined by the following claims.

What is claimed is:

1. A skin rejuvenation serum, comprising:
   deionized water;
   3.5%-6.0% by weight Vitamin C in a form of Magnesium Ascorbyl Phosphate;
   0.5%-2.0% by weight Hyaluronic Acid in a form of low-molecular-weight of 800000-1500000 Da Sodium Hyaluronate;
   0.1%-0.3% by weight Succinic Acid in a form of Sodium Succinate; and
   0.3%-1.0% by weight preservative.

2. The serum of claim 1, wherein the preservative is dehydroacetic acid.

3. The serum of claim 1, further comprising an excipient that is any of:
   0.05%-5.0% by weight Hydrolyzed collagen;
   0.01%-5.0% by weight Allantoin;
   0.01%-5.0% by weight Jade Snail Extract;
   0.5%-10.0% by weight Vitamin E in a form of Tocopherol Acetate;
   15-20% by weight Witch Hazel;
   0.1%-5.0% by weight Urea;
   0.01%-1.0% by weight Barberries Extract; and
   50-20,000 IU/g and <2% of total weight of Vitamin A.

4. A skin rejuvenation serum, comprising:
deionized water;
8-10% by weight Magnesium Ascorbyl Phosphate;
1.0%-2% by weight low-molecular-weight Sodium Hyaluronate of 800000-1500000 Da;
0.3%-0.5% by weight Sodium Succinate Hexahydrate;
0.05%-5.0% by weight Hydrolyzed collagen; and
about 0.5% by weight preservative in a form of dehydroacetic Acid.

5. The serum of claim 1, wherein the Sodium Succinate is Sodium Succinate Hexahydrate.

6. The serum of claim 1, wherein the Sodium Hyaluronate is 0.5%-1.0% by weight.

7. The serum of claim 1, further comprising an excipient that is any of:
0.01%-5.0% by weight Allantoin; and
0.01%-5.0% by weight Jade Snail Extract.

8. The serum of claim 1, further comprising an excipient that is any of:
15-20% by weight Witch Hazel;
0.1%-5.0% by weight Urea;
0.01%-1.0% by weight Barberries Extract.

9. A skin rejuvenation serum, comprising:
deionized water;
8-10% by weight Sodium Ascorbyl Phosphate;
1.0%-2% by weight low-molecular-weight Sodium Hyaluronate of 800000-1500000 Da;
0.3%-0.5% by weight Sodium Succinate Hexahydrate;
0.05%-5.0% by weight Hydrolyzed collagen;
50-20,000 IU/g and <2% of total weight of Vitamin A; and
about 0.5% by weight preservative in a form of dehydroacetic Acid.

* * * * *